United States Patent
Mukaide et al.

(10) Patent No.: US 8,588,366 B2
(45) Date of Patent: Nov. 19, 2013

(54) X-RAY IMAGING APPARATUS AND X-RAY IMAGING METHOD

(75) Inventors: Taihei Mukaide, Atsugi (JP); Kazuhiro Takada, Kawasaki (JP); Kazunori Fukuda, Fujisawa (JP); Masatoshi Watanabe, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 257 days.

(21) Appl. No.: 13/060,739

(22) PCT Filed: Oct. 19, 2009

(86) PCT No.: PCT/JP2009/068297
§ 371 (c)(1),
(2), (4) Date: Feb. 25, 2011

(87) PCT Pub. No.: WO2010/047401
PCT Pub. Date: Apr. 29, 2010

(65) Prior Publication Data
US 2011/0158389 A1    Jun. 30, 2011

(30) Foreign Application Priority Data

Oct. 24, 2008  (JP) .................. 2008-273859
Jun. 1, 2009   (JP) .................. 2009-132096

(51) Int. Cl.
*G01N 23/04*  (2006.01)
(52) U.S. Cl.
USPC ............................................ 378/62; 378/154
(58) Field of Classification Search
USPC .................................. 378/62, 154
See application file for complete search history.

(56) References Cited

U.S. PATENT DOCUMENTS

| 3,755,672 | A | 8/1973 | Edholm et al. ............... 250/322 |
| 4,481,419 | A | 11/1984 | Persyk ...................... 250/363.06 |
| 7,945,018 | B2 | 5/2011 | Heismann et al. ............... 378/62 |
| 2010/0318302 | A1 | 12/2010 | Mukaide et al. .................. 702/28 |
| 2011/0103549 | A1* | 5/2011 | Mukaide et al. .................. 378/62 |

FOREIGN PATENT DOCUMENTS

| CN | 101011254 | 8/2007 |
| JP | 08-211518 | 8/1996 |
| JP | 2002-102215 | 4/2002 |
| JP | 2003-010162 | 1/2003 |
| JP | 2004-317299 | 11/2004 |
| WO | WO 2008/029107 | 3/2008 |

OTHER PUBLICATIONS

Office Action issued Jul. 5, 2012, in counterpart European Application No. 09744782.5.

(Continued)

*Primary Examiner* — Courtney Thomas
(74) *Attorney, Agent, or Firm* — Fitzpatrick, Cella, Harper & Scinto

(57) ABSTRACT

An X-ray imaging apparatus for obtaining information on a phase shift of an X-ray caused by an object comprises: an splitting element for splitting spatially an X-ray emitted from an X-ray generator unit into X-ray beams; an attenuator unit having an arrangement of attenuating elements for receiving the X-ray beams split by the splitting element; and an intensity detector unit for detecting intensities of X-ray beams attenuated by the attenuator unit; and the attenuating element changing continuously the transmission amount of the X-ray depending on the X-ray incident position on the element.

20 Claims, 11 Drawing Sheets

(56) References Cited

OTHER PUBLICATIONS

Office Action issued Jul. 24, 2012, in counterpart P.R. China Application No. 200980141289.6 with translation.

Y. Kagoshima et al., "Scanning Differential-Phase-Contrast Hard X-Ray Microscopy with Wedge Absorber Detector", *Japanese Journal of Applied Physics*, vol. 43, No. 11A, pp. L 1449-L 1451 (2004).

Office Action dated Mar. 26, 2013, issued by Korean Patent Office in counterpart Korean Application 10-2011-7011036, with translation.

Office Action dated Apr. 7, 2013, issued in counterpart Chinese Patent Application No. 200980141289.6, with translation.

English translation of the Office Action of Dec. 20, 2012, issued in counterpart Korean Patent Application No. 10-2011-7011036.

* cited by examiner

X-RAY IMAGING APPARATUS AND X-RAY IMAGING METHOD

TECHNICAL FIELD

The present invention relates to an X-ray imaging apparatus, and an X-ray imaging method.

BACKGROUND ART

Nondestructive inspection with a radiation ray is widely conducted in industries, medical treatments, and so forth.

An X-ray, for example as a kind of the radiation rays, is an electromagnetic ray having a wavelength in the range from about 0.01 Å to 10 nm ($10^{12}$ to $10^8$ m). The X-ray having a shorter wavelength (about 2 keV or higher) is called a hard X-ray, and the X-rays having a longer wavelength (about 0.1 keV to about 2 keV) is called a soft X-ray.

The X-ray absorption contrast method is employed practically, for example, for inspection of an internal crack in iron and steel or baggage security inspection by utilizing the difference in the absorptive power of the highly penetrative X-ray.

On the other hand, for detection of an object having a less difference in the density from the surrounding medium and causing less contrast of X-ray absorption, an X-ray phase contrast imaging method is effective which detects phase shift of the X-ray by the object. Such an X-ray phase contrast imaging method is being studied for imaging of polymer blends and to medical treatment, and so forth.

Of various X-ray phase contrast imaging methods, the refraction contrast method disclosed in Patent Document 1 below utilizes a refraction effect resulting from the phase shift caused by an object.

This refraction contrast method picks up an image by a fine focus X-ray source with a detector placed at a large distance from the object. This refraction contrast method obtains the edge-enhanced image of the object by the X-ray refraction effect by the object.

Further, this refraction contrast method, which utilizes the refraction effect, does not necessarily require a highly coherent X-ray like a synchrotron radiation, which is different from usual X-ray imaging method.

On the other hand, Patent Document 2 discloses an imaging apparatus which has a mask to shield an X-ray at the edge portions of the pixels of the detector. By placing the mask to be irradiated partly by an X-ray in the absence of an object, a shift of the position of the X-ray caused by the refraction effect of the object can be detected as an intensity change of the X-ray.

[Prior Art Documents]
[Patent Documents]
[Patent Document 1] Japanese Patent Application Laid-Open No. 2002-102215
[Patent Document 2] International Patent Application Laid-Open No. 2008/029107

DISCLOSURE OF THE INVENTION

However, in the refraction contrast method disclosed in Patent Document 1, the angle of the X-ray refraction caused by the refraction effect of the object is very small, so that the detector should be placed at a sufficiently large distance from the object to obtain an image of the object with the edge-enhanced. Therefore the refraction contrast method requires inevitably a larger size of the detection apparatus.

The present invention intends to provide an X-ray imaging apparatus and an X-ray imaging method to solve the above shortcomings of the refractivity contrast method.

The present invention is directed to an X-ray imaging apparatus for obtaining information on a phase shift of an X-ray caused by an object, comprising:
an splitting element for splitting spatially an X-ray emitted from an X-ray generator unit into X-ray beams;
an attenuator unit having an arrangement of attenuating elements for receiving the X-ray beams split by the splitting element; and
an intensity detector unit for detecting intensities of X-ray beams attenuated by the attenuator unit; and
the attenuating element changing continuously the transmission amount of the X-ray depending on the X-ray incident position on the element.

The apparatus can have a calculation unit for calculating a differential phase contrast image or a phase contrast image of the object from the X-ray intensity information detected by the intensity detector unit.

The attenuating element can have a thickness changing continuously in a direction perpendicular to an incident X-ray.

The attenuating element can be in a shape of a triangular prism.

The attenuating element can have a density varying continuously in a direction perpendicular to the incident X-ray.

The attenuating element can be in a shape which gives positive a second-order differential value of the optical path length in the attenuating element with respect to the X-ray incident position.

The apparatus can have a movement mechanism for moving synchronously the X-ray generator unit, the splitting element, the attenuator unit, and the intensity detector unit.

The present invention is directed to a method for X-ray imaging with an X-ray imaging apparatus, comprising:
splitting an X-ray spatially; and
collecting information on an X-ray phase shift caused by an object, by use of an attenuator unit having an arrangement of attenuating elements, from the intensity of an X-ray which has transmitted through the attenuating elements; and
the attenuating element changing continuously the transmission amount of the X-ray corresponding to the X-ray incident position in the element.

The present invention is directed to an X-ray imaging apparatus, comprising:
an X-ray generator unit for generating an X-ray;
an attenuator unit having an arrangement of a plurality of attenuating elements having each an absorptive power gradient changing continuously the transmission amount of the X-ray in accordance with an intensity distribution of the X-ray which has transmitted through an object; and
an X-ray intensity detector for detecting the intensity of the X-ray which has been attenuated by the attenuator unit.

The present invention is directed to a method for X-ray imaging with an X-ray imaging apparatus, which employs an attenuator unit having an arrangement of a plurality of attenuating elements having each an absorptive power gradient changing continuously the transmission amount of the X-ray in accordance with an intensity distribution of the X-ray which has transmitted through an object to detect a change in intensity distribution of the X-ray passed through the attenuating element.

The present invention provides an X-ray imaging apparatus and X-ray imaging method which can solve the problems in the conventional refraction contrast method.

Further features of the present invention will become apparent from the following description of exemplary embodiments with reference to the attached drawings.

BEST MODE FOR CARRYING OUT THE INVENTION

In the embodiments of the present invention, an attenuator unit constituted of an arrangement of plural attenuating elements having respectively an absorptive power gradient (or transmittance gradient) is employed to obtain information on a change of an X-ray intensity distribution or a positional shift of the X-ray beam by a refraction effect.

The attenuating element having an absorptive power gradient (or transmittance gradient) herein signifies an element in which the absorption amount (or transmission amount) of the X-ray continuously varies depending on the X-ray intensity distribution or the X-ray incident position. Such an attenuating element can be constituted by changing the shape continuously or stepwise. Otherwise the attenuating elements may be constituted by changing the amount of the absorption (or transmission) of the X-ray per unit volume. Incidentally, the wording "continuously" in the specification of the present application may include the meaning of the wording "in stages".

The X-ray imaging apparatus and the X-ray imaging method of the present invention are described below with reference to specific embodiments.

(Embodiment 1)

Embodiment 1 describes a constitution of an X-ray imaging apparatus for picking up an image of an object from a phase shift of an X-ray.

Figure 15:
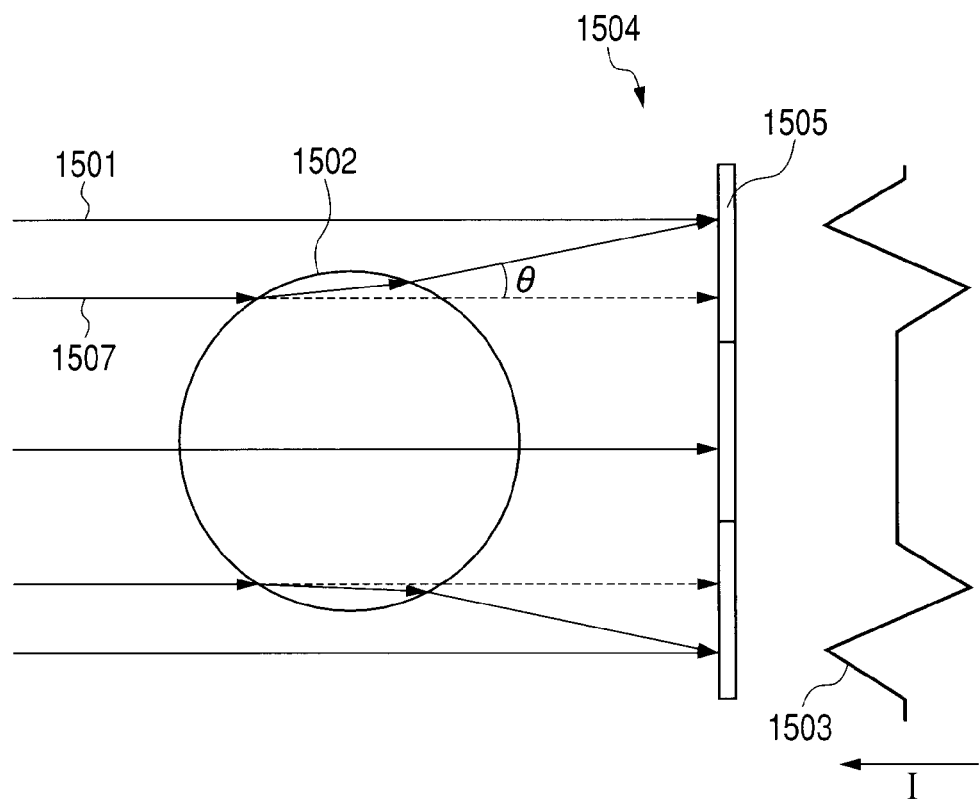
FIG. 15 illustrates refraction of an X-ray by a substance.

FIG. 15 illustrates schematically refraction of an X-ray beam by transmission through a substance. Here, the refraction index of the substance to the X-ray is slightly lower than 1.

Thus in the case illustrated in FIG. 15, A X-ray beam 1507 is refracted outward from substance 1502 by transmission through substance 1502 (X-ray beam 1507 being refracted upward in FIG. 15).

The X-ray beam which has transmitted through substance 1502 comes to overlap with X-ray 1501 which has traveled along the outside of substance 1502 to increase the X-ray intensity at the overlapping position, whereas on the imaginary extended line of the X-ray beam 1507 to be refracted at the incident position on the substance, the X-ray intensity is lower. Consequently, the intensity distribution 1503 of the transmitted X-ray is increased at the edge of substance 1502 as illustrated in FIG. 15.

Since the refraction angle θ of the X-ray is very small, the distance between the substance and the detector should be made longer to obtain an edge-enhanced profile line in consideration of the pixel size of the detector. Therefore, in the refraction contrast method described in the above Patent Document 1, the apparatus is larger inevitably owing to the necessary long distance between the object and the detector for enlarging the image.

With the detector placed at a shorter distance from the object, the size of one pixel 1505 of detector 1504 is larger than the intensity pattern in the transmitted X-ray intensity distribution 1503 to cancel each other to uniformize the intensity within the one pixel. This makes impossible to obtain an edge-enhanced image of the substance.

Therefore, this Embodiment is characterized by an attenuator unit having an absorptive power gradient in the respective attenuating elements for detecting a pattern of an X-ray intensity with a short distance between the object and the detector.

Figure 1:
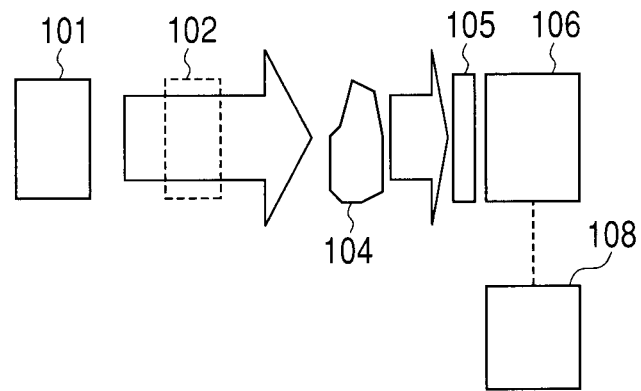
FIG. 1 illustrates a constitution of the X-ray imaging apparatus in Embodiment 1 of the present invention.

FIG. 1 illustrates a constitution of the X-ray imaging apparatus of this Embodiment.

The X-ray generated by X-ray source 101 as an X-ray generator unit has its phase shifted by object 104 to come to be refracted. The refracted X-ray is introduced to attenuator unit 105. The X-ray which has transmitted through attenuator unit 105 is detected by detector 106 as the intensity detector unit. The information obtained by detector 106 is output to display unit 108 like a monitor.

Object 104 includes human bodies, and other materials such as inorganic materials and inorganic-organic composite materials. Incidentally, a movement mechanism (not shown in the drawing) may be provided additionally for moving object 104. By moving object 104 suitably, images at specified spots of object 104 can be obtained.

As detector 106, various types of X-ray detectors can be used, including indirect type ones and direct type ones, such as an X-ray flat panel detector, an X-ray CCD camera, and a direct conversion type X-ray two-dimensional detector.

Detector 106 may be placed near attenuator unit 105 or at a certain distance from it. Attenuator unit 105 can be incorporated into detector 106.

For using a monochromatic X-ray, a monochromator unit 102 may be provided between X-ray source 101 and object 104. Monochromator unit 102 includes a combination of slits, and an X-ray multilayer mirror.

Figure 2:
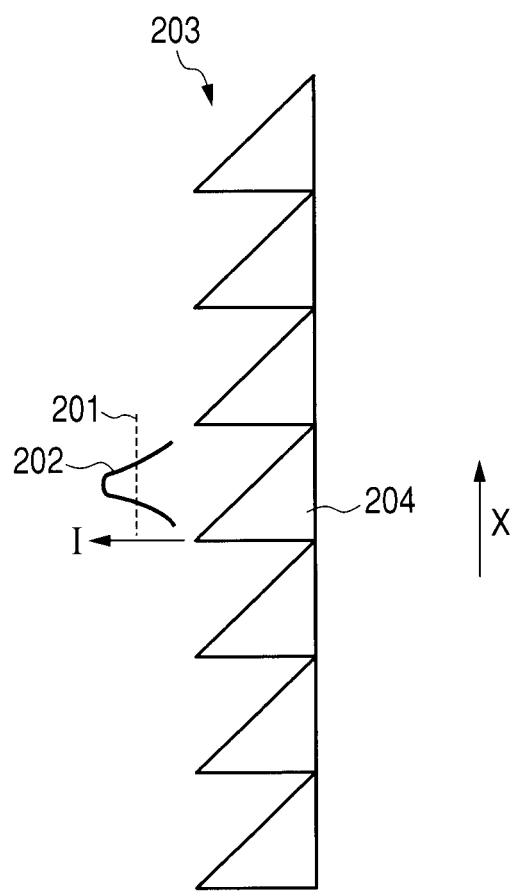
FIG. 2 illustrates schematically a part of the attenuator unit in Embodiment 1 of the present invention.

Next, attenuator unit 105 is described in more detail. FIG. 2 illustrates schematically a part of attenuator unit 105. In this drawing, attenuator unit 203 is constituted of attenuating elements 204 having respectively a triangular prism shape having a thickness changing in a direction perpendicular to the incident X-ray.

With such a constitution, the optical path length of the transmitted X-ray in attenuating element 204 is varied in the X direction. Thus, attenuating element 204 has an absorptive power gradient by which the absorption (or transmission) is varied depending on the X-ray intensity distribution or the X-ray incident position. The attenuating elements 204 may be formed by working of a plate-shaped member.

In FIG. 2, the numeral 201 denotes an intensity distribution of a reference X-ray introduced to attenuating element 204 in the absence of object 104, and the numeral 202 denotes an intensity distribution of a reference X-ray changed by refraction by object 104 and introduced to attenuating element 204.

The intensity of the X-ray detected by one pixel of the detector is an integrated intensity within the one pixel regardless of the intensity distribution of the X-ray introduced to the one pixel. However, attenuating elements 204 which will continuously change the transmitted X-ray intensity in the X direction enables conversion of the X-ray intensity distribution change caused by refraction by object 104 into a change in the transmitted X-ray intensity.

For example, in FIG. 2, an upward shift of intensified position 202 in the drawing increases the intensity of the transmitted X-ray, whereas a downward shift of intensified position 202 in the drawing decreases the intensity of the transmitted X-ray. Therefore, a minute refraction effect can be detected as an X-ray intensity distribution by comparing the X-ray intensity detected in the absence of object 104 with the X-ray intensity detected in the presence of object 104.

Such a constitution enables detection of a minute change of the intensity distribution within one pixel of detector 106. This makes unnecessary to place detector 106 at a long distance from object 104, and enables a smaller size of the apparatus. Further, with this constitution, a finer change of the intensity distribution by the refraction can be detected by placing detector 106 at a longer distance from object 104.

With this technique, a higher coherent X-ray need not be used since the phase shift is detected by the refraction effect of the X-ray.

Figure 4A:
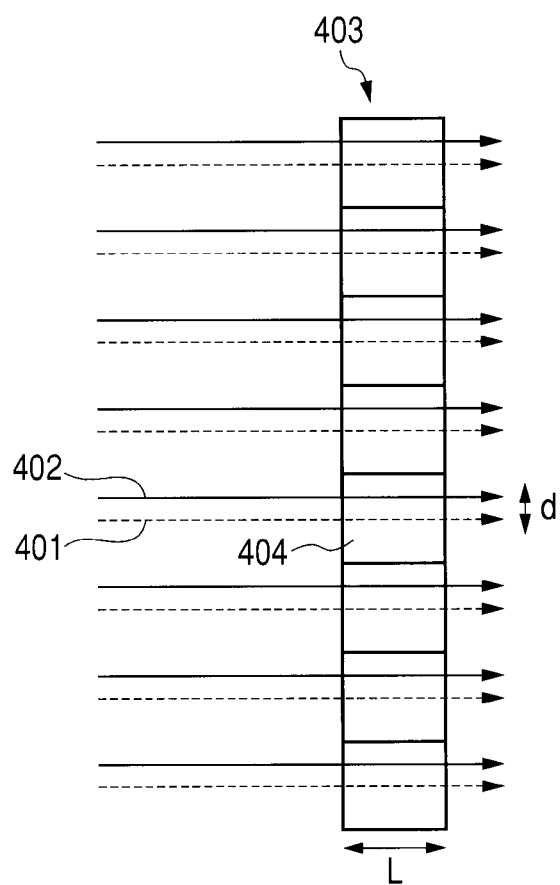
FIGS. 4A and 4B illustrate a part of the attenuator unit in Embodiment 2 of the present invention.
Figure 4B:
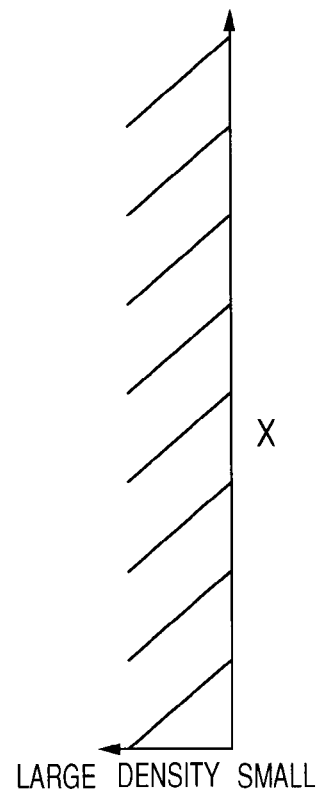

In the above description, the attenuating element has a uniform effective absorption coefficient and has a shape changing continuously. However, the attenuating element needs only to have an absorptive power gradient so as to change the absorption amount (transmission amount) of the X-ray in a certain direction. For example, an attenuating element having the density varying continuously in a direction perpendicular to the incident X-ray as illustrated in FIGS. 4A and 4B, which will be described later, is useful also for the X-ray imaging apparatus of this Embodiment.

Further, the absorptive power gradient of the attenuating element need not be continuous as shown in FIG. 2, but the amount of absorption (transmission) may be changed stepwise. For example, the shape of the element may be changed stepwise, or the density of the element may be changed stepwise.

The absorptive power gradient in the attenuating element may be formed in two or more directions for obtaining the change of the X-ray intensity distribution. For example, the absorptive power gradient may be formed in an X direction and a Y direction within one attenuating element to measure the phase gradients in two directions. For the measurement in two or more directions, the element may be in a shape of a pyramid or a cone.

The absorptive power gradient is not limited to be uniform among the attenuating elements. A first type of attenuating elements having the gradient in an X direction and a second type of attenuating elements having the gradient in a Y direction may be arranged alternately on a plane to measure the phase gradient two-dimensionally.

Otherwise, attenuating elements having a gradient in an X direction and those having a gradient in a Y direction may be laminated. That is, a first layer may be formed from a first attenuator unit having an absorptive power gradient in an X direction, and a second layer may be formed from a second attenuator unit having an absorptive power gradient in a Y direction.

To prevent blurring of the image by scattered X-ray from attenuator unit 105, a grid like the one conventionally used in roentgen imaging may be placed between attenuator unit 105 and detector 106.

(Embodiment 2: Constitution Employing Splitting Element)

This Embodiment 2 describes an X-ray imaging apparatus and an X-ray imaging method for obtaining a phase contrast image as X-ray phase shift information. This Embodiment is different from Embodiment 1 in that an element for splitting the X-ray is employed.

Figure 16A:
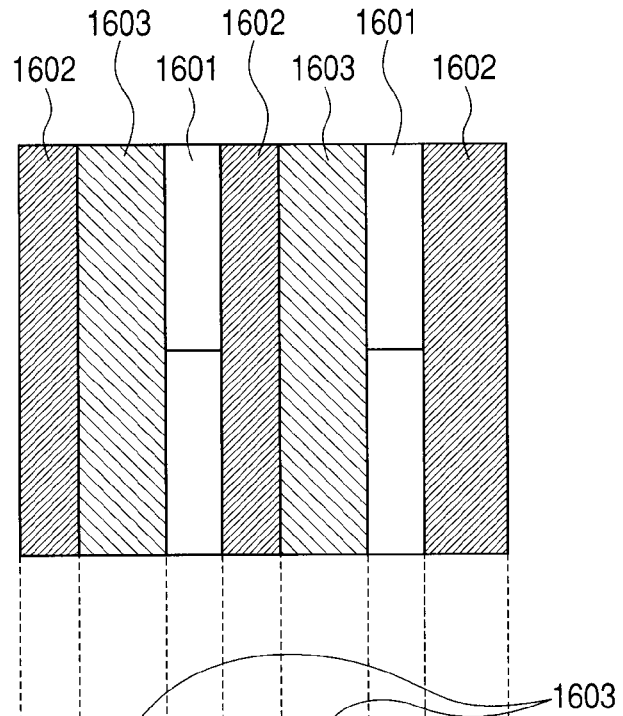
FIGS. 16A and 16B are drawings for describing the problem in Patent Document 2.
Figure 16B:
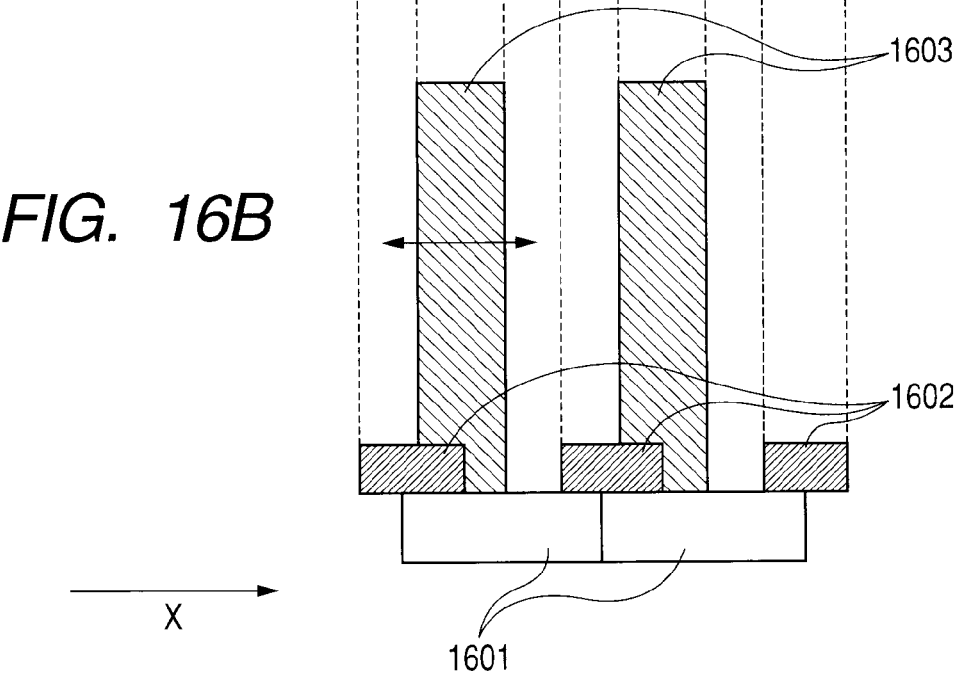

The imaging apparatus disclosed in the above cited Patent Document 2 employs an optical element for splitting the X-ray and a mask for shielding the X-ray at the edge portions of the elements of the detector. FIGS. 16A and 16B illustrate an example of a part of the detector described in Patent Document 2. FIG. 16A is a view of the part of the detector from X-ray introduction side, and FIG. 16B is a view taken from the side perpendicular to the X-ray introduction direction.

Mask 1602 is provided to shield the X-ray beams at the edge portions of respective pixels 1601 of the detector. Projected X-ray beams 1603 are introduced to the respective pixels with parts of the X-ray beams shielded by masks 1602. With such an arrangement, incident X-ray beams 1603 are deflected to change the incident positions on pixel 1601 by the refraction effect. This deflection changes the intensities of the X-ray beams introduced to the pixels by shielding by masks 1602. The refraction effect can be measured by detecting the change of the X-ray intensity.

In the method disclosed in Patent Document 2, mask 1602 is employed to shield the X-ray. Therefore, when the region of the irradiation of X-ray 1603 is entirely on mask 1602, the deflection of the X-ray cannot be detected disadvantageously. Further, deflection of incident X-ray 1603 within the region of mask 1602 cannot be detected. That is, the method of Patent Document 2 has a problem of the insensible region.

Therefore, this Embodiment 2 describes an apparatus and method which enables a smaller size of the apparatus in comparison with the refraction contrast method and which has less insensible region in comparison with the method described in Patent Document 2.

Figure 3:
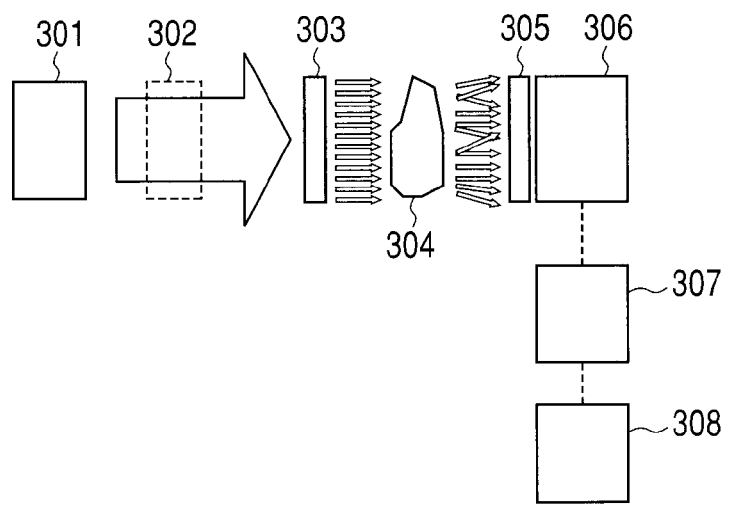
FIG. 3 illustrates a constitution of the X-ray imaging apparatus in Embodiment 2 of the present invention.

FIG. 3 illustrates a constitution of the X-ray imaging apparatus of this Embodiment.

The X-ray emitted from X-ray source 301 as the X-ray generator unit is split by splitting element 303 spatially into X-ray beams. That is, X-ray functions as a sampling mask having apertures as described in Patent Document 2. X-ray transmitted through splitting element 303 forms flux of X-ray. Splitting element 303 may be in a shape of a line-and-space slit array, or in a shape of a two-dimensional hole arrangement.

The slit of in splitting element 303 need not penetrate through the base plate, insofar as the slit allows the X-ray to pass through. Splitting element 303 is formed from a material having a high X-ray absorptive power, including Pt, Au, Pb, Ta, and W; and compounds containing such an element.

The pitch of the line-and-space of the X-ray split by splitting element 303 at the position of detector 306 is not smaller than the pixel size of detector 306. That is, the size of the pixel constituting the X-ray detector unit is not larger than the spatial pitch of the X-ray split by splitting element 303.

The X-ray beams split spatially by splitting element 303 are refracted by object 304. The respective X-ray beams are introduced into attenuator unit 305. The X-ray beams which have passed through attenuator unit 305 are subjected to measurement of the X-ray intensity by detector 306. The information on the X-ray obtained by detector 306 is processed arithmetically with calculator unit 307 and is output to display unit 308 like a monitor.

Monochromator unit 302, object 304, the movement mechanism for moving the object 304, detector 306, the grid, and so forth may be the same as those employed in Embodiment 1.

Attenuator unit 305 is described more specifically.

FIG. 4A illustrates schematically a part of attenuator unit 305.

Reference X-ray beam 401 is an X-ray beam split in the absence of object 304, and is preferably introduced to the center of X-ray attenuator element 404 in the X direction. X-ray beam 402 denotes an X-ray beam refracted by the presence of object 304. Attenuator unit 403 is constituted of an arrangement of a plurality of attenuating elements 404.

As illustrated in FIG. 4B, attenuating element 404 has the density distributed continuously in the X direction (perpendicular to the incident X-ray beam). The density change of attenuating element 404 in FIGS. 4A and 4B changes the degree of the absorption (transmittance) of the X-ray, the higher density portion allowing less the penetration of the X-ray. That is, attenuating element 404 has an absorptive power gradient to continuously change the absorption (transmission) of the X-ray depending on the incident position of the X-ray.

The intensity of reference X-ray 401 which has passed through attenuating element 404 is represented by Equation 1 below:

$$I = I_0 e^{-(\frac{\mu}{\rho})\rho_0 L} \qquad \text{Equation 1}$$

In the above Equation, $I_0$ denotes the intensity of the X-ray which has been split spatially by splitting element 303; $\mu/\rho$ denotes the effective mass absorption coefficient of attenuating element 404; $\rho_0$ denotes the density of attenuating element 404 at the portion where reference X-ray beam 401 passes through attenuating element 404; and L denotes the thickness of attenuating element 404.

The intensity of X-ray beam 402 which has been refracted by object 304 and has passed through attenuating element 404 is represented by Equation 2 below:

$$I' = I_0 A e^{-(\frac{\mu}{\rho})\rho' L} \qquad \text{Equation 2}$$

In the above equation, A denotes the transmittance of the X-ray through object 304; $\rho'$ denotes the density of attenuating element 404 at the portion where X-ray beam 402 passes through attenuating element 404. From the above Equations 1 and 2, the difference between the density of the portion where the reference X-ray beam 401 passes through attenuating element 404 and the density of the portion where shifted X-ray beam 402 passes through the attenuating element 404 is represented by Equation 3 below:

$$\rho_0 - \rho' = \frac{1}{(\frac{\mu}{\rho})L} \ln\left(\frac{I'}{IA}\right) \qquad \text{Equation 3}$$

With object 304 which absorbs the X-ray extremely little, the transmittance A is approximately 1. With an object having a non-negligible absorption effect, the transmittance, the transmittance A can be derived from imaging in the absence of attenuating element 305.

On the other hand, since the density distribution in the X-ray absorption body is known, the positional shift (d) on attenuator unit 305 can be derived from the density difference indicated by the above Equation 3.

That is, the fine positional shift caused by refraction by object 304 can be estimated from the relation between the detected intensities of reference X-ray 401 and X-ray 402.

Next, an arithmetic processing in this Embodiment is described below.

Figure 5:
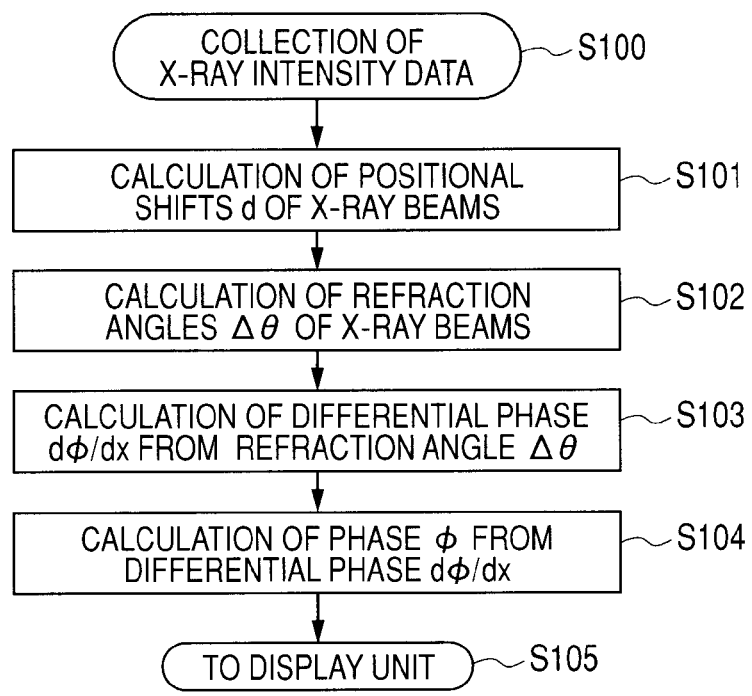
FIG. 5 is a flow chart of a process of calculation in Embodiment 2 of the present invention.

FIG. 5 is a flow chart of the arithmetic processing.

Firstly in the first step S100, information on the intensities of the respective X-ray beams which have passed through attenuator unit 305 is obtained.

In the second step S101, processor unit 307 calculates the positional shift d of the respective X-ray beams relative to reference X-ray 401 from the information on the intensities in the respective pixels in the direction perpendicular to the slit pitch direction.

The positional shift (d) can be estimated by Equation 3. Since the density distribution in the X-ray absorption body is known, the positional shift (d) on attenuator unit 305 can be estimated from the density difference shown by Equation 3.

Otherwise, a table of the correspondence relation between the transmitted X-ray intensity and the positional shift (d) is stored in processor unit 307 or the like, and the positional shift (d) can be estimated from the measured intensity by reference to the data table. This data table can be prepared, for respective attenuating elements 404, by moving attenuator unit 305 or splitting element 303 and detecting the transmitted X-ray intensity at each of the positions. In preparing the data table, in place of moving splitting element 303, a single slit having the same slit width as splitting element 303 may be employed, and the transmitted X-ray intensity is detected at the respective positions of attenuating elements 404.

In the third step S102, the refraction angles ($\Delta\theta$) of the respective X-ray beams are calculated. The refraction angle ($\Delta\theta$) of the respective X-ray beams is calculated from the positional shift (d) and the distance (Z) between object 304 and attenuator unit 305 according to Equation 4 below:

$$\Delta\theta = \tan^{-1}\left(\frac{d}{Z}\right) \qquad \text{Equation 4}$$

The refraction angle ($\Delta\theta$) and the differential phase ($d\phi/dx$) are in the relation of Equation 5.

$$\frac{d\phi}{dx} = \frac{2\pi}{\lambda}\Delta\theta \qquad \text{Equation 5}$$

In the Equations, λ denotes the wavelength of the X-ray. When the X-ray is a continuous wave, λ denotes an effective wavelength.

Next, in the fourth step S103, a differential phase (dφ/dx) is calculated for the respective pixels in the direction perpendicular to the slit pitch direction according to the above equation 5 to obtain the differential phase information.

Next, in the fifth step S104, the each of the differential phases (dφ/dx) obtained by the above calculation is integrated in the X direction to obtain the phase information φ. In the step S105, the calculated differential phase contrast image and the phase contrast image can be displayed in display unit 108.

With the above constitution, a minute positional shift of the X-ray can be detected, which enables a shorter distance between object 304 and detector 306. Thus the apparatus can be miniaturized in comparison with that of the refraction contrast method disclosed in Patent Document 1. Further, the use of splitting element 303 enables quantification of the differential phase quantity, and the phase quantity. Furthermore, this constitution does not have an insensible region owing to use of a transmission type of attenuator unit 305 which does not have an X-ray shielding region.

With the above constitution having a longer distance between object 304 and detector 306, a finer positional shift of the X-ray can be detected.

Further, since the phase shift is detected by utilizing the X-ray refraction effect, the X-ray need not be highly coherent.

(Embodiment 3)

This Embodiment 3 describes a constitution of an X-ray imaging apparatus which employs an attenuator unit which is different from the one in Embodiment 2. The basic constitution of the apparatus in this Embodiment is the same as the one illustrated in FIG. 3 for description of Embodiment 2.

Figure 6:
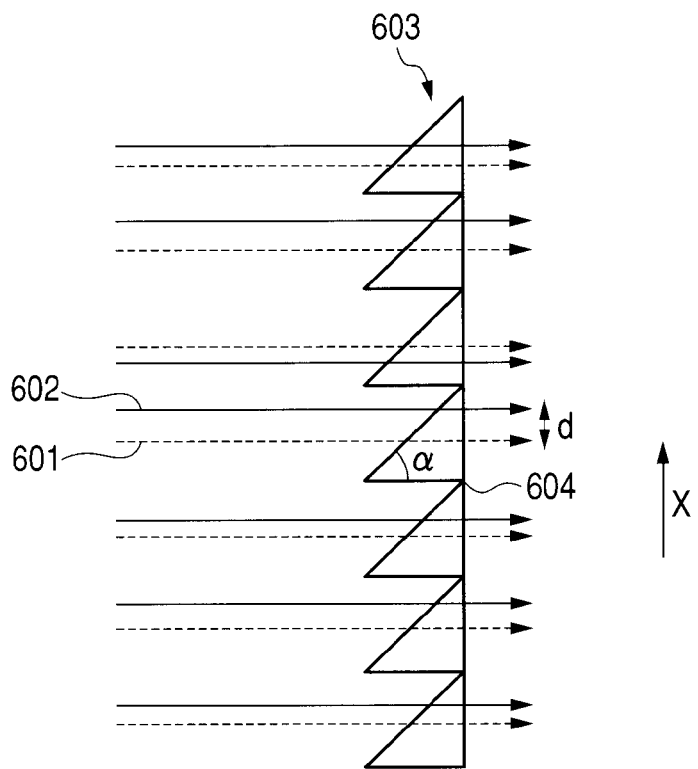
FIG. 6 illustrates schematically a constitution in Embodiment 3 employing another type of attenuator unit in place of the attenuator unit of Embodiment 2.

FIG. 6 illustrates schematically a constitution of Embodiment 3.

The reference numeral 601 denotes an X-ray beam which is split in the absence of object 304. This reference X-ray 601 is preferably introduced to the center of attenuating element 604 in the X direction. The numeral 602 denotes an X-ray beam refracted by object 304.

As illustrated in FIG. 6, attenuator unit 603 is constituted of an arrangement of attenuating elements 604 each having a shape of a triangular prism. This attenuating element 604 has a uniform effective ray-absorption coefficient, and has the thickness changing continuously in the direction perpendicular to the X-ray introduction.

Since attenuating element 604 is in a shape of a triangular prism, the optical path length of the transmitting X-ray varies within attenuating element 604 in the X direction, which varies the amount of the absorption (transmission) of the X-ray depending on the X-ray incident position in the X direction.

The intensity of the reference X-ray 601 which has passed through attenuating element 604 is represented by Equation 6 below:

$$I = I_0 e^{-\mu l_0} \quad \text{Equation 6}$$

In the above equation, the symbol $I_0$ denotes the intensity of the X-ray beam split spatially by splitting element 303, the symbol μ denotes an effective linear absorption coefficient of attenuating element 604, and the symbol $l_0$ denotes the optical path length of reference X-ray beam 601 through attenuating element 604.

On the other hand, the intensity of the X-ray beam 602 which has been refracted by object 304 and has passed through attenuating element 604 is represented by Equation 7 below:

$$I' = I_0 A e^{-\mu l} \quad \text{Equation 7}$$

In the above equation, the symbol A denotes the transmittance of the X-ray through object 304, the symbol l denotes the optical path length of X-ray beam 602 through attenuating element 604.

From Equation 6, Equation 7, and the apex angle α of attenuating element 604, the positional shift d of the X-ray beam caused by the object on attenuator unit 305 is represented by Equation 8 below:

$$d = \frac{1}{\mu} \ln\left(\frac{I'}{IA}\right) \tan\alpha \quad \text{Equation 8}$$

When the X-ray absorption effect of object 304 is extremely small, the value of A is 1, and when the absorption effect is not negligible, the value of A can be derived from the imaging in the absence of attenuator unit 305.

That is, a minute positional shift d caused by refraction by object 304 can be derived from the relation between the detected intensities of reference X-ray beam 601 and the refracted X-ray beam 602.

The triangular prism of attenuating element 604 enables the estimation of the positional shift d based on the ratio of reference X-ray 601 to refracted X-ray 602 at any position of attenuating element 604.

The X-ray which has transmitted through attenuator unit 305 is detected by detector 306. From the detected data, the differential phase (dφ/dx) and the phase (φ) of the X-ray in the respective elements in the direction perpendicular to the slit pitch direction with calculator unit 307 similar to the one employed in Embodiment 2. The differential phase contrast image and the phase contrast image are displayed by displaying unit 308.

Without Equation 8, the positional shift d can be estimated from intensity information in practical measurement with reference to a data table prepared separately regarding the relation of the detected intensity to the positional shift d. This data table can be prepared by detecting the intensity of the transmitted X-ray beam by displacing attenuator unit 305 or splitting element 303 for each of attenuating elements 604. In the preparation of the data table, instead of displacing splitting element 303, a single slit having the same width as splitting element 303 may be employed for detecting the transmitted X-ray intensity on the positions of attenuating elements 604.

Such a constitution enables detection of extremely minute positional shift of an X-ray beam, making unnecessary the long distance between object 304 and detector 306, and enables miniaturization of the imaging apparatus. Further, attenuator unit 305 of this constitution, which is of a transmission type containing no X-ray-shielding region, gives no insensible region.

With this constitution, a finer positional shift of the X-ray beam by refraction can be detected by lengthening the distance between object 304 and detector 306.

Further, since the phase shift is detected by the effect of refraction of X-ray beam, the X-ray need not be highly coherent.

(Embodiment 4: Attenuating Element in Curved Shape)

This Embodiment 4 describes an attenuating element which is different in the shape from the one of Embodiment 3.

Figure 7A:
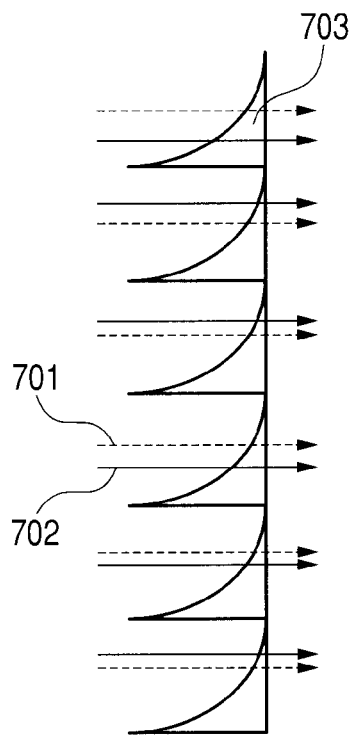
FIGS. 7A and 7B are drawings for describing the attenuator unit and the attenuating element in Embodiment 4 of the present invention.
Figure 7B:
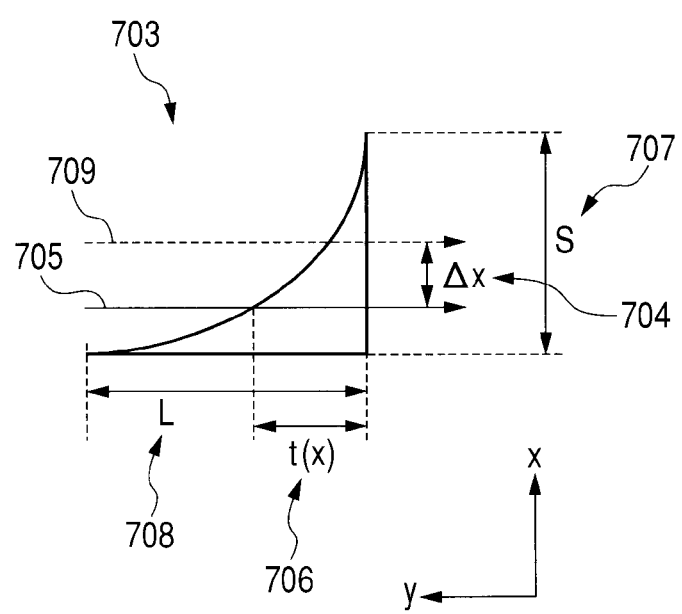

FIG. 7A illustrates a constitution of the attenuator unit of Embodiment 4. FIG. 7B illustrates a constitution of an attenuating element of the attenuator unit.

The attenuating element which has a shape changing continuously with a positional shift of refracted X-ray beam 702 from the position of reference X-ray beam 701 is capable of detecting the positional shift, by detector 305 as the X-ray intensity change. However, when the change of the optical path length is linear to the positional shift of the refracted X-ray, the detected X-ray intensity changes remarkably exponentially relative to the positional shift, and effective detection of the positional shift can be conducted only in a limited narrow range. Therefore in this Embodiment, the variation of the optical path length is not linear to the positional shift of the refracted X-ray but in a shape giving a positive value of the second-order differential thereof.

FIG. 7B is a schematic enlarged view of attenuating element 703. In FIG. 7B, the direction of the positional shift by refraction is taken in the X-axis direction, and the optical path of the X-ray beam perpendicular thereto is taken in the Y-axis direction.

The X-ray beam which has transmitted through the object is shifted by $\Delta x$ (reference numeral 704) from reference X-ray beam 709 to refracted X-ray beam 705. The attenuating element 703 is in a shape which gives a positive second-order differential of the optical path length $t(x)$ 706 of the refracted X-ray beam transmission through attenuating element 703 with respect to the X-ray beam incident position, $d^2t(x)/dx^2$. In particular, when the change of optical path length 706 is exponential, the optical path length $t(x)$ is represented by Equation 9 below.

$$t(x) = AR \cdot s[1 - \ln(X+1)/\ln(s+1)] \quad \text{Equation 9}$$

wherein the symbol s denotes the length of attenuating element 703 in the x-axis direction, AR denotes the aspect ratio of attenuating element 703. The symbol s in the above equation is denoted in FIG. 7B by the reference numeral 707. The aspect ratio AR is represented by Equation 10 below:

$$AR = L/s \quad \text{Equation 10}$$

wherein L denotes the length in the y-axis direction denoted by the reference numeral 708. The symbol s (reference numeral 707) is an integral multiple of the resolution of the X-ray detector unit, when the attenuator unit and the X-ray detector unit are placed close to each other, whereas when they are not close to each other, the value of s is adjusted so that the projection of attenuating element 703 onto the detection face is an integral multiple of the resolution of the X-ray detector unit.

When the change of optical path length 706 is linear, the optical path length $t(x)$ is represented by Equation 11 below:

$$t(x) = AR(s-x) \quad \text{Equation 11}$$

The second order differential of this optical path length $t(x)$ is zero.

The intensity $I(x)$ of the X-ray measured by the detector is represented by Equation 12 with respect to the dynamic range DR of the detector:

$$I(x) = DR \cdot \exp(-t(x)/l_{ex}) \quad \text{Equation 12}$$

wherein $l_{ex}$ denotes an attenuation length of the material of attenuating element 703 to the X-ray. On the other hand, when the change of the optical path length in attenuating element 703 is exponential, the intensity $I(x)$ of the X-ray detected by the detector is represented by Equation 13 below:

$$I(x) = DR \cdot \exp[-AR \cdot s\{1 - \ln(x+1)/\ln(s+1)\}/l_{ex}]$$
$$= DR \cdot e^{-a}(x+1)^b \quad \text{Equation 13}$$

wherein a, and b are represented respectively by Equation 14 and Equation 15:

$$a = AR \cdot s/l_{ex} \quad \text{Equation 14}$$

$$b = a/\ln(s+1) = AR \cdot s/(l_{ex} \cdot \ln(s+1)) \quad \text{Equation 15}$$

By adjusting the value of b to be close to 1 by selecting the aspect ratio and material of the attenuating element 703, the change of the detected intensity becomes linear. By adjusting the intensity change to be linear, the change of the detected intensity can be made gradual in comparison with the exponential rapid change of the intensity.

Next, the exponential change of optical path length 706 of in attenuating element 703 (the intensity change being linear) is compared with the linear change of the optical path length (the intensity change being exponential).

In the calculation below, the X-ray emitted from the X-ray generator unit is a characteristic X-ray of Mo. The length s (reference numeral 707) in the x-axis direction, and the dynamic range DR of attenuating element 703 are respectively depend on the resolution and the dynamic range of detector 306. In this Embodiment, the detector employed is an X-ray flat panel detector, and s=100 µm, DR=5000 cps, and integration time of the detection is one second.

For attenuating element 703, an intensity change by a factor of about 100 between the both ends of the element is intended for a sufficient intensity change for the incident position shift, and the AR is selected to be about 1 for workability. That is, a material of attenuation length $l_{ex}$ of about 22 µm is selected according to the equation: $l_{ex} = -\ln(1/100)/(AR \cdot s)$. An example of such a material for the attenuating element is Cu of $l_{ex} = 22.8$ µm.

Here, an effective detection range for the detection intensity $I(x)$ is the range in which the differential of $I(x)$ is larger than the square root of $I(x)$ which is a statistical error. The ratio of the effective detection range to the length s in the X-axis direction is represented by "eff". Therefore, when the detection of the positional shift is effective throughout the entire region of the attenuating elements 703, eff=1.

Figure 8:
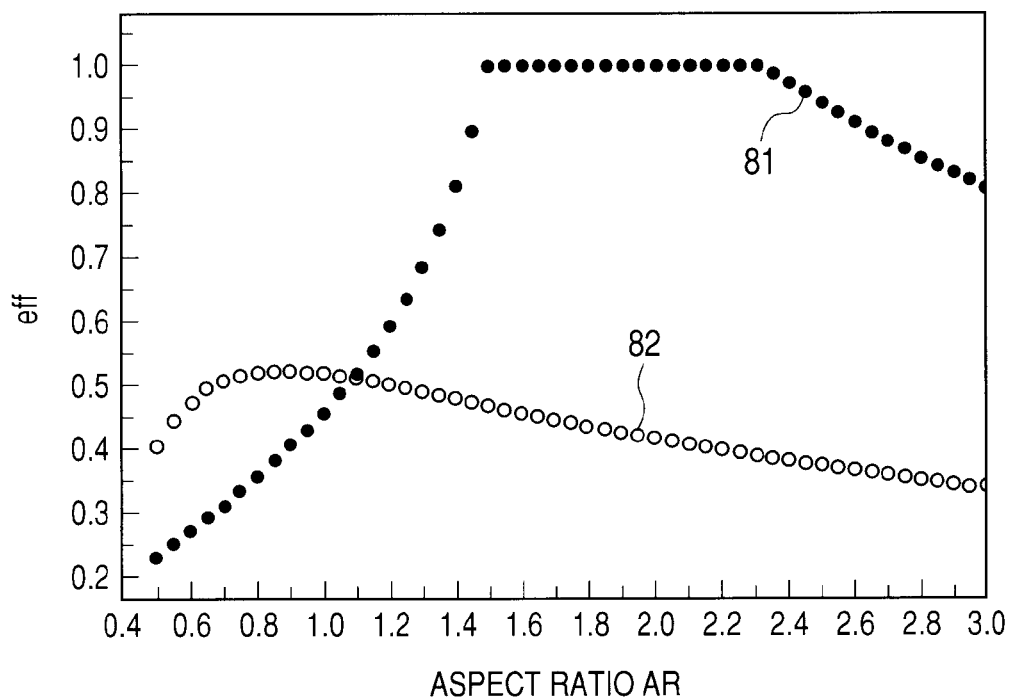
FIG. 8 is a graph for comparison of optical path length changes of an exponential function type with that of a linear function type.

In FIG. 8, plot line 81 shows dependence of the eff on aspect ratio AR for a case in which the change of the optical path length 706 of attenuating element 703 is of a logarithmic function type (Equation 9), and plot line 82 for a case in which the change is of a linear function type (Equation 11).

From the graph, when the optical path length change is of a logarithmic function type, eff=1 can be achieved by adjusting the aspect ratio AR in the range of from about 1.5 to 2.5, whereas when the optical path change is of a linear function type, the improvement of eff is limited to about eff=0.5, even if the aspect ratio AR is adjusted.

Figure 9A:
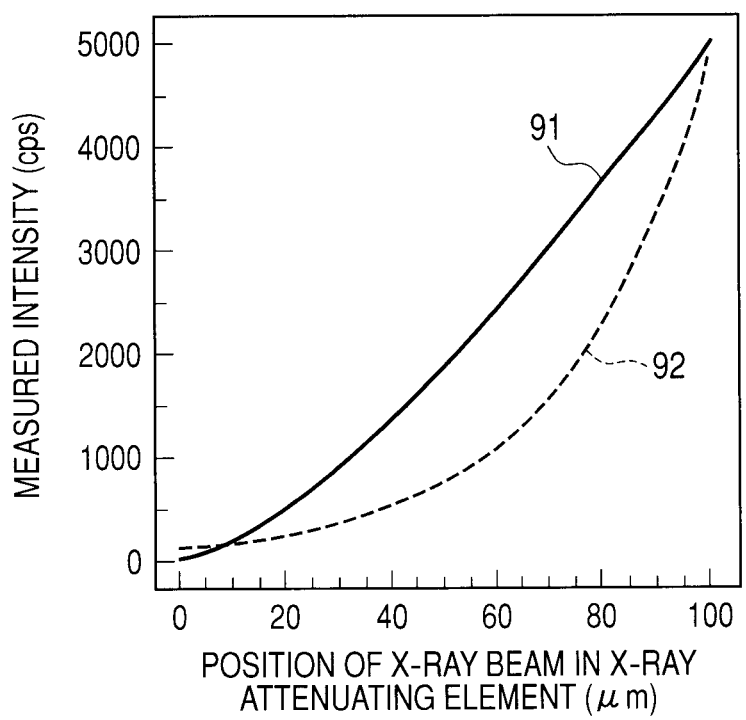
FIGS. 9A and 9B are graphs for comparison of optical path length changes of an exponential function type with that of a linear function type.

In FIG. 9A, plot line 91 shows the measured intensity change for a logarithmic function type change of optical path length 706 at the aspect ratio of 1.5, and plot line 92 shows the change for a linear function type change of optical path length 706 at the aspect ratio of 0.85.

Figure 9B:
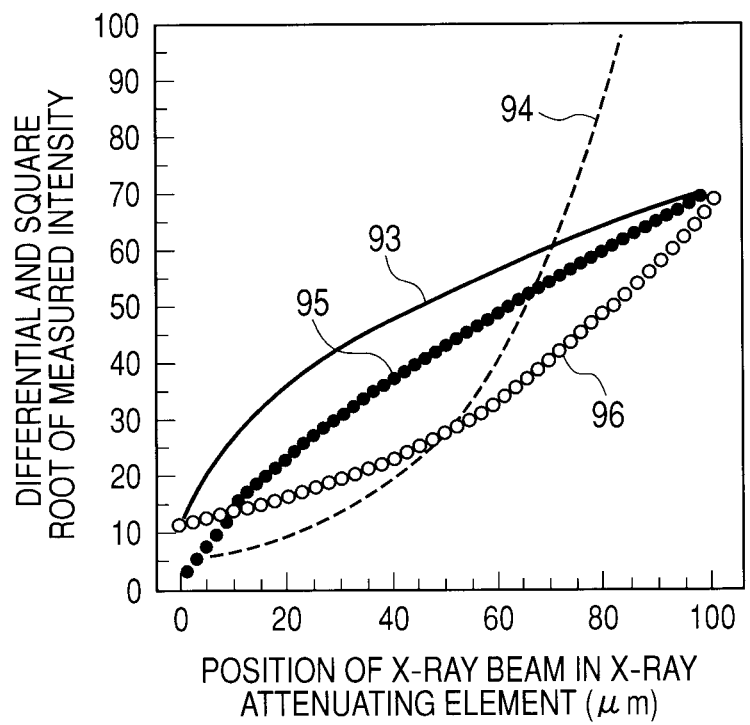

FIG. 9B shows differentials and square roots (statistical error) of the intensity change shown in FIG. 9A. Plot line 93 shows differential of the intensity change for the logarithmic function type, and plot line 95 shows the statistical error thereof. Plot line 94 shows differential of the intensity change of the linear function type, and plot line 96 shows the statistical error thereof.

As shown in the above graphs, the measured intensity change by the aspect ratio of the logarithmic type is gradual in comparison with that of the linear type, and the differential of the measured intensity change is more than the statistical error throughout the entire region of the element: that is, eff=1.

When the change of optical path length is of a logarithmic function type, even when the aspect ratio AR is fixed to 1, eff=1 can be achieved by adjusting the attenuation length $l_{ex}$ to be about 1.4.

The attenuation length $l_{ex}$ can be adjusted by a pure metal like Cu, but can be adjusted also by an alloy or a metal mixture. The alloy therefore is preferably a solid solution. However, a material is useful which has the microstructure sufficiently small in the length in the x-axis direction and in comparison with the sectional size of the X-ray beam. The pure metal, alloy or metal mixture may have the density changed by porous structure to adjust the attenuation length $l_{ex}$. The porous structure has preferably a pore size sufficiently small relative to the length s (reference numeral 707) and the sectional size of refracted X-ray beam 702.

Figure 10:
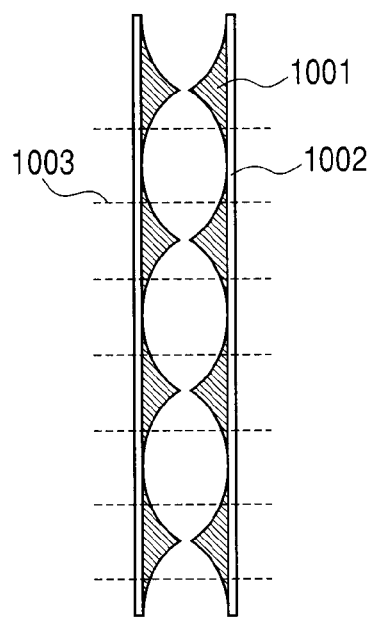
FIG. 10 is a drawing for describing the attenuator unit in Embodiment 4.

The attenuating elements may be constituted by counterposed cylindrical faces as illustrated in FIG. 10. For example, X-ray attenuating parts 1001 formed from Cu are supported by supporting plates 1002. The supporting plates 1002 may be constituted of a resin having a thickness which will not cause X-ray absorption practically. In the attenuator unit illustrated in FIG. 10, between the adjacent attenuating elements, the positional shifts of the refracted X-ray beams from reference X-ray 1003 in the same direction are detected as intensity changes in a reversed sense. In this attenuating elements, the second order differential of the optical path change is positive.

(Embodiment 5: Computed Tomography)

This Embodiment 5 describes a constitution of an apparatus for obtaining a three-dimensional phase distribution based on the principle of computed tomography (CT).

Figure 11:
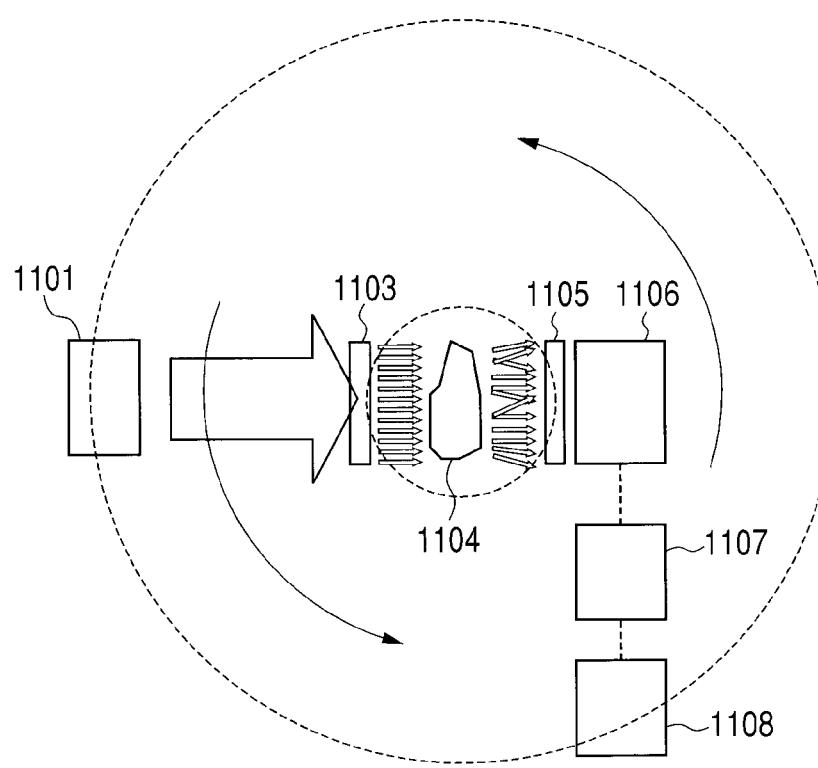
FIG. 11 illustrates schematically a constitution for computed tomography (CT) in Embodiment 5 of the present invention.

FIG. 11 illustrates schematically a constitution of the CT apparatus in this Embodiment.

In FIG. 11, the reference numerals denote the following members: 1101, an X-ray source; 1103, an splitting element; 1104, an object; 1105, an attenuator unit; 1106, an X-ray detector; 1107, a calculator unit; and 1108, a display unit.

In the CT apparatus of this Embodiment, X-ray source 1101, splitting element 1103, attenuator unit 1105, and X-ray detector 1106 are movable synchronously around object 1104 by a movement mechanism.

The X-ray beams split spatially by splitting element 1103 are projected to object 1104, and the transmitted X-ray beams are introduced into attenuator unit 1105.

Attenuator unit 1105 detects a minute positional shift of the split X-ray caused by refraction by object 1104. The X-ray which has transmitted through attenuator unit 1105 is detected by X-ray detector 1106.

Projection data of object 1104 is collected by moving X-ray source 1101, splitting element 1103, attenuator unit 1105, and X-ray detector 1106 synchronously around object. Otherwise, the object 1104 is rotated, while X-ray source 1101, splitting element 1103, attenuator unit 1105, and X-ray detector 1106 are fixed, to collect the projection data.

Next, the calculation processing in this Embodiment is described below.

Figure 12:
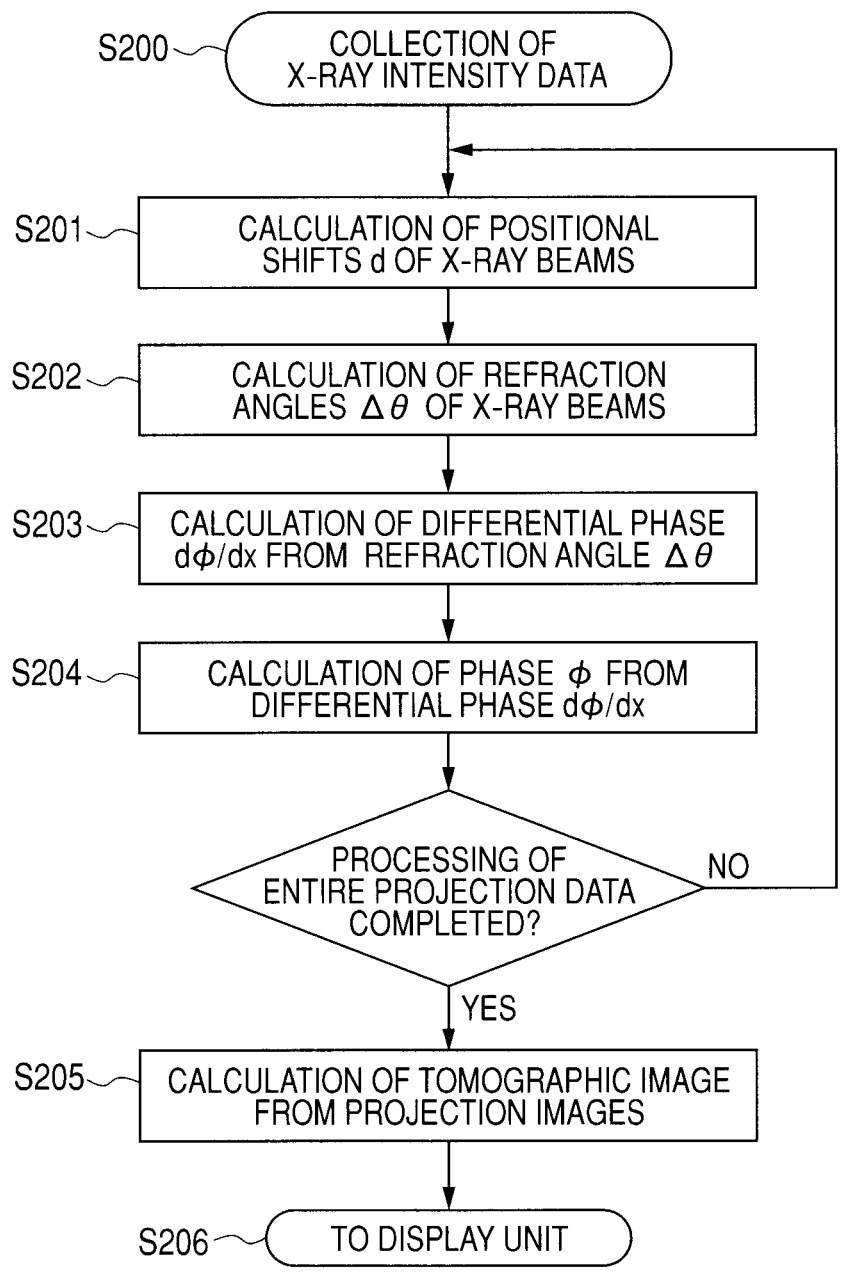
FIG. 12 is a flow chart of calculation process in Embodiment 5 of the present invention.

FIG. 12 is a flow chart of the calculation processing.

In the first step S200, information on the intensities of the X-ray beams which have transmitted through attenuator unit 1105 are collected.

In the second step S201, positional shifts (d) of the X-ray beams from the reference X-ray beams are calculated from the intensities of the respective X-ray beams.

In the third step S202, the refraction angles ($\Delta\theta$) of the X-ray beams are derived from the positional shifts (d) and the distance (Z) between object 1104 and attenuator unit 1105.

In the fourth step S203, the differential phases ($d\phi/dx$) of the respective X-ray beams are calculated from the refraction angles ($\Delta\theta$).

In the fifth step S204, the phase ($\phi$) is calculated by integration of the differential phases ($d\phi/dx$) in the X-direction.

The above series of the operations from S201 to S204 are repeated for the entire projection data.

Next, in the sixth step S205, a tomographic image is obtained from the phase contrast images of the entire projection data by image reconstruction method (e.g., a filter back-projection method) in computed tomography.

In step S206, the tomographic image is displayed by display unit 1108.

This constitution enables miniaturization of the apparatus, and precludes the necessity of use of a highly coherent X-ray, by utilizing the refraction effect. This CT apparatus enables formation of a three-dimensional image of an object nondestructively.

EXAMPLES

Examples of the present invention are described below.

Example 1

Example 1 describes a constitution of the X-ray imaging apparatus of the present invention.

Figure 13:
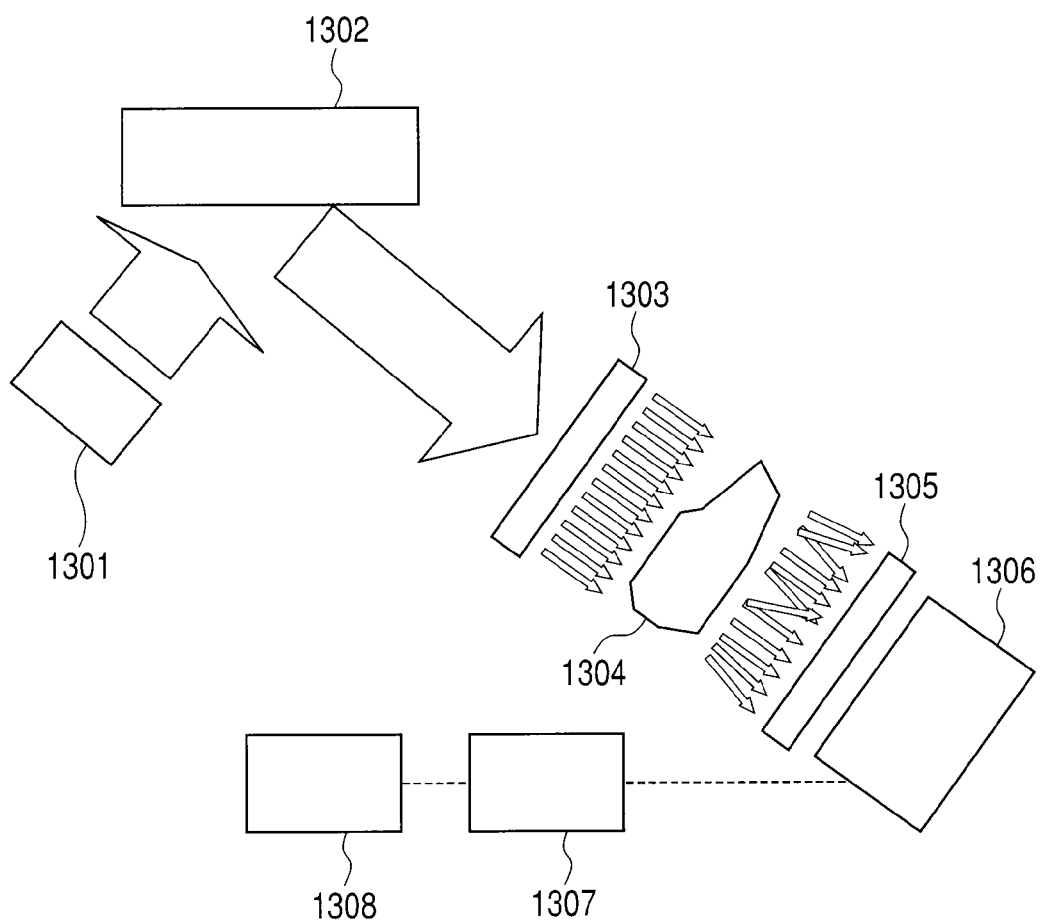
FIG. 13 illustrates a constitution of the X-ray imaging apparatus in Example 1 of the present invention.

FIG. 13 illustrates schematically a constitution of this Example.

In FIG. 13, the reference numerals denote the following members: 1301, an X-ray source; 1302, a monochromator; 1303, an splitting element; 1304, an object; 1305, an attenuator unit; 1306, an X-ray detector; 1307, a processor unit; and 1308, a display unit.

In this Example, X-ray source 1301 is a Mo-target rotating anticathode type of X-ray generating apparatus.

For monochromating the X-ray, a monochromator 1302 of highly oriented pyrolytic graphite (HOPG) is used, and the characteristic X-ray fraction of Mo is extracted.

The monochromatic X-ray from monochromator 1302 is split spatially by splitting element 1303 placed 100 cm apart from the X-ray source.

This splitting element 1303 is an arrangement of slits of 40 µm wide on W of 100 µm thick at a slit pitch of 150 µm on attenuator unit 1305.

In place of W as the material for the splitting element, Au, Pb, Ta, Pt, or the like may be used.

The X-ray beams from splitting element 1303 are projected onto object 1304. Then, X-ray beams which have transmitted through object 1304 are introduced to attenuator unit 1305 placed 50 cm apart from object 1304.

Attenuator unit 1305 has a structure in which triangular prisms of Ni of 75 µm high are arranged at a pitch of 150 µm on a carbon base plate of 1 mm thick.

The attenuator unit is placed so that the X-ray beams split by splitting element 1303 are introduced respectively to the center of the triangular prism in the pitch direction.

The intensities of the X-ray beams which have transmitted through attenuator unit 1305 are detected by X-ray detector 1306 as the detector unit placed near to attenuator unit 1305.

X-ray detector 1306 is a flat panel type detector having pixels of a size of 50 µm×50 µm. The sum of the X-ray intensities at three pixels in the prism pitch direction is taken as the X-ray intensity of one attenuating element.

The same imaging is conducted in the absence of the object 1304. From the change of the intensities of the X-ray beams by the presence of the object, the positional shift (d) of the respective X-ray beams is calculated by processor unit 1307 based on a database for X-ray transmittance at positions of the attenuator unit of preliminary measurement. Therefrom, the refraction angle (Δθ) in each of the attenuation elements is calculated according to Equation 4 in the direction perpendicular to the slit pitch direction.

From the refraction angle (Δθ), the differential phase quantity is calculated according to Equation 5, and the differential phase quantity is integrated spatially to obtain the phase distribution image.

The X-ray differential phase contrast image and the X-ray phase contrast image obtained by processor unit 1307 are displayed in a PC monitor as display unit 1308.

Example 2

This Example 2 describes another constitution of the X-ray imaging apparatus of the present invention.

Figure 14:
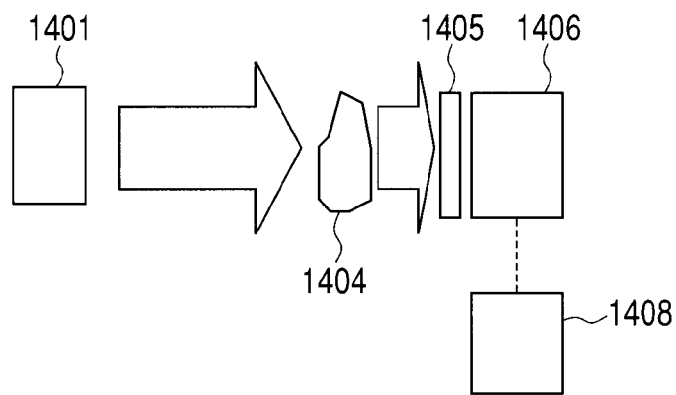
FIG. 14 illustrates a constitution of the X-ray imaging apparatus in Example 2 of the present invention.

FIG. 14 illustrates schematically a constitution of this Example.

In FIG. 14, the reference numerals denote the following members: 1401, an X-ray source; 1404, an object; 1405, an attenuator unit; 1406, an X-ray detector; and 1408, a display unit.

In this Example, X-ray source 1401 is a Mo-target rotating anticathode type of X-ray generating apparatus.

The X-ray generated by X-ray source 1401 is projected to object 1404 placed 100 cm apart from X-ray source 1401. The X-ray which has transmitted through object 1404 is introduced to attenuator unit 1405 placed 50 cm apart from object 1404.

Attenuator unit 1405 has triangular prisms of Ni of 75 µm high arranged on a carbon base plate of 1 mm thick at a pitch of 150 µm.

The intensities of the X-ray beams which have transmitted through attenuator unit 1405 are detected by X-ray detector 1406 as the detector unit closely placed to attenuator unit 1405.

X-ray detector 1406 is a flat panel type detector having pixels of a size of 50 µm×50 µm.

The image of the object is obtained by mathematical processing from the image formed in the absence of the object in the same manner, and the obtained image is displayed on a PC monitor as display unit 1408.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2008-273859 filed Oct. 24, 2008, and No. 2009-132096 filed Jun. 1, 2009 which are hereby incorporated by reference herein in their entirety.

The invention claimed is:

1. An X-ray imaging apparatus for obtaining information on a phase shift of X-rays caused by an object, comprising:
    a splitting element for splitting spatially X-rays emitted from an X-ray generator unit into X-ray beams;
    an attenuator unit having an arrangement of attenuating elements for receiving the X-ray beams split by said splitting element; and
    an intensity detector unit for detecting intensities of X-ray beams attenuated by said attenuator unit,
    said attenuating element changing continuously the transmission amount of the X-rays depending on the X-ray incident position on said attenuating element.

2. The X-ray imaging apparatus according to claim 1, further comprising a calculation unit for calculating a differential phase contrast image or a phase contrast image of the object from the X-ray intensity information detected by said intensity detector unit.

3. The X-ray imaging apparatus according to claim 1, wherein said attenuating element has a thickness changing continuously in a direction perpendicular to incident X-rays.

4. The X-ray imaging apparatus according to claim 3, wherein said attenuating element is in a shape of a triangular prism.

5. The X-ray imaging apparatus according to claim 1, wherein said attenuating element has a density varying continuously in a direction perpendicular to the incident X-rays.

6. The X-ray imaging apparatus according to claim 1, wherein said attenuating element is in a shape which makes positive a second-order differential value of the optical path length in said attenuating element with respect to the X-ray incident position.

7. The X-ray imaging apparatus according to claim 1, further comprising a movement mechanism for moving synchronously said X-ray generator unit, said splitting element, said attenuator unit, and said intensity detector unit.

8. A method for X-ray imaging with an X-ray imaging apparatus, comprising the steps of:
    splitting X-rays spatially; and
    collecting information on an X-ray phase shift caused by an object, by use of an attenuator unit having an arrangement of attenuating elements, from the intensity of X-rays which have been transmitted through the attenuating elements,
    the attenuating element changing continuously the transmission amount of the X-rays corresponding to the X-ray incident position in the attenuating element.

9. An X-ray imaging apparatus, comprising:
    an X-ray generator unit for generating X-rays;
    an attenuator unit having an arrangement of a plurality of attenuating elements having each an absorptive power gradient changing continuously the transmission amount of the X-rays in accordance with an intensity distribution of the X-rays which have been transmitted through an object; and
    an X-ray intensity detector for detecting the intensity of the X-rays which have been attenuated by said attenuator unit.

10. A method for X-ray imaging with an X-ray imaging apparatus, which employs an attenuator unit having an arrangement of a plurality of attenuating elements having each an absorptive power gradient changing continuously the transmission amount of the X-rays in accordance with an intensity distribution of the X-rays which have been transmitted through an object to detect a change in intensity distribution of the X-rays that have passed through the attenuating element, said method comprising the steps of:

generating the X-rays; and
collecting information on an X-ray phase shift caused by the object.

11. An X-ray imaging apparatus comprising:
an attenuator unit having an arrangement of attenuating elements for receiving X-ray beams which have been transmitted through an object; and
an intensity detector unit for detecting intensities of X-ray beams attenuated by said attenuator unit,
wherein said intensity detector unit has a plurality of pixels, and
wherein said attenuating elements are configured such that transmission amounts of the X-ray beams change continuously or stepwise in accordance with incident positions of the X-ray beams.

12. The X-ray imaging apparatus according to claim 11, further comprising:
a splitting element for splitting spatially an X-ray emitted from an X-ray generator unit into the X-ray beams,
wherein said attenuating elements are configured to receive the X-ray beams split by said splitting element.

13. The X-ray imaging apparatus according to claim 12, wherein said attenuating elements are configured to receive the X-ray beams after the split X-ray beams have been transmitted through the object.

14. The X-ray imaging apparatus according to claim 11, further comprising a calculation unit for calculating a differential phase contrast image or a phase contrast image of the object from the X-ray intensity information detected by said intensity detector unit.

15. The X-ray imaging apparatus according to claim 11, wherein said attenuating elements have a thickness changing in a direction perpendicular to an incident X-ray.

16. The X-ray imaging apparatus according to claim 11, wherein said attenuating elements have a density varying in a direction perpendicular to the incident X-ray.

17. The X-ray imaging apparatus according to claim 11, wherein said attenuating elements each are in a shape which gives a positive $d^2t(x)/dx^2$ value when the incident position of the X-ray is taken as x and an optical path length of the attenuating element is taken as $t(x)$.

18. The X-ray imaging apparatus according to claim 11, further comprising a movement mechanism for moving said attenuator unit and said intensity detector unit synchronously.

19. An X-ray imaging method comprising:
detecting, by a detector unit which has an arrangement of pixels, an intensity of X-ray beams which have been transmitted through an attenuator unit having an arrangement of attenuating elements for receiving X-ray beams which have been transmitted through an object,
wherein the attenuator unit is configured such that transmission amount of the X-ray changes continuously or stepwise in accordance with an incident position of the X-ray.

20. The X-ray imaging method according to claim 19, further comprising
splitting an X-ray spatially,
wherein the attenuator unit is configured to receive split X-ray beams.

* * * * *